(12) United States Patent
Shoji et al.

(10) Patent No.: US 9,758,496 B2
(45) Date of Patent: *Sep. 12, 2017

(54) METHOD OF USING A CYCLIC CARBODIIMIDE

(75) Inventors: Shinichiro Shoji, Iwakuni (JP); Hirotaka Suzuki, Iwakuni (JP)

(73) Assignee: TEIJIN LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/133,028

(22) PCT Filed: Dec. 15, 2009

(86) PCT No.: PCT/JP2009/071192
§ 371 (c)(1),
(2), (4) Date: Jun. 6, 2011

(87) PCT Pub. No.: WO2010/071212
PCT Pub. Date: Jun. 24, 2010

(65) Prior Publication Data
US 2011/0237755 A1    Sep. 29, 2011

(30) Foreign Application Priority Data

Dec. 15, 2008  (JP) ................................. 2008-318598

(51) Int. Cl.
| | | |
|---|---|---|
| C08G 63/00 | (2006.01) | |
| C08L 67/00 | (2006.01) | |
| C07D 273/08 | (2006.01) | |
| C07D 245/02 | (2006.01) | |
| C07D 498/10 | (2006.01) | |
| C08G 63/91 | (2006.01) | |
| C08G 69/48 | (2006.01) | |

(52) U.S. Cl.
CPC .......... *C07D 273/08* (2013.01); *C07D 245/02* (2013.01); *C07D 498/10* (2013.01); *C08G 63/91* (2013.01); *C08G 63/912* (2013.01); *C08G 69/48* (2013.01)

(58) Field of Classification Search
None
See application file for complete search history.

(56) References Cited

U.S. PATENT DOCUMENTS

| | | | |
|---|---|---|---|
| 2006/0276617 A1 | 12/2006 | Yano et al. | |
| 2008/0161554 A1* | 7/2008 | Dai et al. | 540/454 |
| 2009/0137748 A1 | 5/2009 | Tanaka et al. | |
| 2009/0318628 A1* | 12/2009 | Tanaka et al. | 525/419 |
| 2011/0160364 A1 | 6/2011 | Toyohara et al. | |

FOREIGN PATENT DOCUMENTS

| | | |
|---|---|---|
| DE | 10004328 A1 | 8/2001 |
| EP | 1640406 A1 | 3/2006 |
| JP | 11-092636 A | 4/1999 |
| JP | 2005-002174 A | 1/2005 |
| JP | 2008-050579 A | 3/2008 |
| JP | 2008-050584 A | 3/2008 |
| WO | 2005/000946 A1 | 1/2005 |
| WO | 2007/091427 A1 | 8/2007 |
| WO | 2008/010355 A1 | 1/2008 |

OTHER PUBLICATIONS

International Preliminary Report on Patentability issued on Jul. 14, 2011 for counterpart application PCT/JP2009/071192.
European Search Report issued on May 7, 2012 for counterpart European application 09833514.4.

* cited by examiner

*Primary Examiner* — Ana Woodward
(74) *Attorney, Agent, or Firm* — Sughrue Mion, PLLC

(57) ABSTRACT

A method of sealing an end of a polymer with a carbodiimide compound without liberating an isocyanate compound. A compound including a cyclic structure having one carbodiimide group whose first nitrogen and second nitrogen are bonded together by a bond group is used as an end-sealing agent for the polymer.

15 Claims, No Drawings

METHOD OF USING A CYCLIC CARBODIIMIDE

TECHNICAL FIELD

The present invention relates to a method of using a cyclic carbodiimide as an end-sealing agent for polymers.

BACKGROUND ART

It has already been proposed to use a carbodiimide compound as an end-sealing agent for a polymer having a terminal acid group such as a carboxyl group so as to suppress the hydrolysis of the polymer (Patent Documents 1 and 2). The carbodiimide compound used in this proposal is a linear carbodiimide compound.

When the linear carbodiimide compound is used as an end-sealing agent for polymers, a compound having an isocyanate group is liberated by a reaction for bonding the linear carbodiimide compound to an end of the polymer to produce a smell peculiar to an isocyanate compound, thereby deteriorating the work environment.

Patent Document 3 discloses a macrocyclic carbodiimide compound. Since this compound is produced as a highly diluted solution, the concentration of the macrocyclic carbodiimide compound is low, whereby it takes many days to react it with a polymer and therefore the utility of the macrocyclic carbodiimide compound as an end-sealing agent for polymers is low. Since the molecular weight of the macrocyclic carbodiimide compound is high with respect to the carbodiimide group, the efficiency of the macrocyclic carbodiimide compound as an end-sealing agent for polymers is low. Further, Patent Document 3 does not take into consideration the reduction of an isocyanate smell produced by the end-sealing of a polymer. This macrocyclic carbodiimide compound has a long chain, is readily decomposed at a high temperature and therefore is not suitable for use as an end-sealing agent for polymers having a high melting point such as polyesters.
(Patent Document 1) JP-A 2008-050584
(Patent Document 2) JP-A 2005-2174
(Patent Document 3) US-A 2008/0161554

DISCLOSURE OF THE INVENTION

It is an object of the present invention to provide a method of sealing an end of a polymer with a carbodiimide compound without liberating an isocyanate compound.

The inventors of the present invention have conducted intensive studies on a carbodiimide compound which does not liberate an isocyanate compound even when it reacts with an end of a polymer. As a result, they have found that a compound having only one carbodiimide group in the cyclic structure does not liberate an isocyanate compound even when it reacts with an end of a polymer. The present invention has been accomplished based on this finding. Further, they have found a method of sealing an end of a polymer efficiently by limiting the number of members of the cyclic structure to a specific range.

That is, the present invention is a method of using a compound including a cyclic structure having one carbodiimide group whose first nitrogen and second nitrogen are bonded together by a bond group (may be referred to as "cyclic carbodiimide compound" hereinafter) as an end-sealing agent for polymers having an acid group. The method of the present invention is a method of suppressing the production of a free isocyanate compound.

The present invention is a method of suppressing the production of a free isocyanate compound when a carbodiimide compound is added to a polymer having an acid group to seal its end, wherein a compound including a cyclic structure having one carbodiimide group whose first nitrogen and second nitrogen are bonded together by a bond group is used as the carbodiimide compound.

BEST MODE FOR CARRYING OUT THE INVENTION

<Cyclic Structure>
In the present invention, the cyclic carbodiimide compound which is used as an end-sealing agent has a cyclic structure. The cyclic carbodiimide compound may have a plurality of cyclic structures.

The cyclic structure has one carbodiimide group (—N═C═N—) whose first nitrogen and second nitrogen are bonded together by a bond group. One cyclic structure has only one carbodiimide group. The number of atoms contained in the cyclic structure is preferably 8 to 50, more preferably 10 to 30, much more preferably 10 to 20, particularly preferably 10 to 115.

The number of atoms contained in the cyclic structure is the number of atoms directly constituting the cyclic structure. For example, in the case of a 8-membered ring, the number of atoms is 8 and in the case of a 50-membered ring, the number of atoms is 50. When the number of atoms contained in the cyclic structure is smaller than 8, the stability of the cyclic carbodiimide compound degrades, thereby making it difficult to store and use the cyclic carbodiimide compound. There is no particular upper limit to the number of members of the ring from the viewpoint of reactivity but it is difficult to synthesize a cyclic carbodiimide compound having more than 50 atoms and its cost may rise sharply. From this point of view, the number of atoms contained in the cyclic structure is preferably 10 to 30, more preferably 10 to 20, particularly preferably 10 to 15.

The molecular weight of the cyclic carbodiimide compound is preferably 100 to 1,000. When the molecular weight is lower than 100, the structural stability and volatility of the cyclic carbodiimide compound may become problematic. When the molecular weight is higher than 1,000, synthesis in a dilution system is required for the production of the cyclic carbodiimide, or the yield lowers, thereby causing a cost problem. From this point of view, the molecular weight of the cyclic carbodiimide compound is more preferably 100 to 750, much more preferably 250 to 750.

The cyclic structure is preferably represented by the following formula (1).

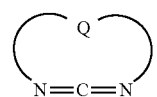

(1)

In the above formula, Q is a divalent to tetravalent bond group which is selected from an aliphatic group, an alicyclic group, an aromatic group or a combination of these and may contain a heteroatom or a substituent. Two out of the valences of this bond group are used to form the cyclic structure. When Q is a trivalent or tetravalent bond group, it is bonded to a polymer or another cyclic structure through a single bond, a double bond, an atom or an atom group.

The bond group is preferably a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof. A bond group having a number of carbon atoms required for the formation of a cyclic structure is selected as the bond group. An example of the combination is an alkylene-arylene group in which an alkylene group and an arylene group are bonded together.

The aliphatic group, alicyclic group and aromatic group constituting the bond group may contain a heteroatom or a substituent. The heteroatom refers to O, N, S or P. Examples of the substituent include an alkyl group having 1 to 20 carbon atoms, aryl group having 6 to 15 carbon atoms, halogen atom, nitro group, amide group, hydroxyl group, ester group, ether group and aldehyde group.

In the present invention, examples of the halogen atom include chlorine atom, bromine atom and iodine atom.

The bond group (Q) is preferably a divalent to tetravalent bond group represented by the following formula (1-1), (1-2) or (1-3).

  (1-1)

  (1-2)

  (1-3)

In the above formulas, $Ar^1$ and $Ar^2$ are each independently a divalent to tetravalent aromatic group having 5 to 15 carbon atoms and may contain a heteroatom or a substituent.

Examples of the aromatic group include an arylene group having 5 to 15 carbon atoms, arenetriyl group having 5 to 15 carbon atoms, and arenetetrayl group having 5 to 15 carbon atoms. Examples of the arylene group (divalent) include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

$R^1$ and $R^2$ are each independently a divalent to tetravalent aliphatic group having 1 to 20 carbon atoms, a divalent to tetravalent alicyclic group having 3 to 20 carbon atoms, a combination thereof, or a combination of the above aliphatic group, the above alicyclic group and a divalent to tetravalent aromatic group having 5 to 15 carbon atoms and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylenes group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These alicyclic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

$X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms or a combination thereof and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These alicyclic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

s and k are each independently an integer of 0 to 10, preferably 0 to 3, more preferably 0 to 1. When s and k are larger than 10, it is difficult to synthesize the cyclic carbodiimide compound and its cost may rise sharply. From this point of view, the integer is preferably selected from 0 to 3. When s or k is 2 or more, $X^1$ or $X^2$ as a recurring unit may differ from another $X^1$ or $X^2$, respectively.

$X^3$ is a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms or a combination thereof and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may contain a substituent. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may contain a substituent. Examples of the substituent include an alkyl group having 1 to 20 carbon atoms, arylene group having 6 to 15 atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

As described above, $Ar^1$, $Ar^2$, $R^1$, $R^2$, $X^1$, $X^2$ and $X^3$ may contain a heteroatom.

When Q is a divalent bond group, all of $Ar^1$, $Ar^2$, $R^1$, $R^2$, $X^1$, $X^2$ and $X^3$ are divalent groups. When Q is a tervalent group. When Q is a tetravalent bond group, one of $Ar^1$, $Ar^2$, $R^1$, $R^2$, $X^1$, $X^2$ and $X^3$ is a tetravalent group, or two of them are tervalent groups.

Compounds represented by the following formulas (a) to (c) are enumerated as examples of the cyclic carbodiimide used in the present invention.

<Cyclic Carbodiimide (a)>

A compound represented by the following formula (2) (may be referred to as "cyclic carbodiimide (a)" hereinafter) is given as the cyclic carbodiimide used in the present invention.

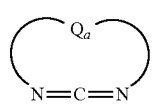

(2)

In the above formula, $Q_a$ is a divalent bond group which is selected from an aliphatic group, an alicyclic group, an aromatic group or a combination of these and may contain a heteroatom or a substituent.

The aliphatic group, alicyclic group and aromatic group are as defined in the above formula (1). In the compound of the formula (2), all of the aliphatic group, alicyclic group and aromatic group are divalent. $Q_a$ is preferably a divalent bond group of the following formula (2-1), (2-2) or (2-3).

 (2-1)

 (2-2)

 (2-3)

In the above formulas, $Ar_a^1$, $Ar_a^2$, $R_a^1$, $R_a^2$, $X_a^1$, $X_a^2$, $X_a^3$, s and k are identical to $Ar^1$, $Ar^2$, $R^1$, $R^2$, $X^1$, $X^2$, $X^3$, s and k defined in the above formulas (1-1) to (1-3), respectively. However, all of them are divalent.

The cyclic carbodiimide (a) is preferably a compound represented by the following formula (2-1-1).

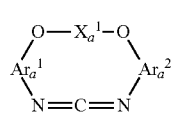

(2-1-1)

In the above formula, $X_a^1$ is an alkylene group having preferably 1 to 20 carbon atoms, more preferably 1 to 10 carbon atoms. Examples of the alkylene group include methylene group, ethylene group, trimethylene group and tetramethylene group.

In the above formula, $Ar_a^1$ and $Ar_a^2$ are each independently an arylene group having 5 to 15 carbon atoms which may be substituted. Examples of the arylene group include phenylene group and naphthalenediyl group. The arylene group may be substituted. The substituent is an alkyl group having 1 to 20 carbon atoms, preferably 1 to 6 carbon atoms. Examples of the substituent include methyl group, ethyl group and propyl group.

The cyclic carbodiimide (a) is preferably a compound represented by the following formula (2-1-1a).

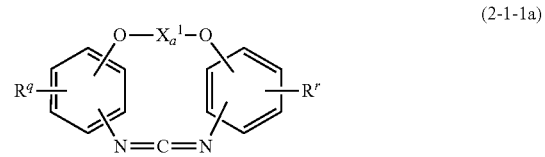

(2-1-1a)

In the above formula, $X_a^1$ is an alkylene group having preferably 1 to 20 carbon atoms, more preferably 1 to 10 carbon atoms, much more preferably 1 to 4 carbon atoms. Examples of the alkylene group include methylene group, ethylene group, trimethylene group and tetramethylene group.

In the above formula, $R^q$ and $R^r$ are each independently an alkyl group having preferably 1 to 20 carbon atoms, more preferably 1 to 6 carbon atoms or hydrogen atom. Examples of the alkyl group include methyl group, ethyl group and propyl group.

The following compounds are enumerated as examples of the cyclic carbodiimide compound (a).

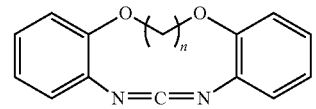

(n is an integer of 1 to 6)

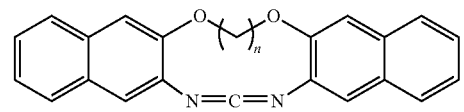

(n is an integer of 1 to 6)

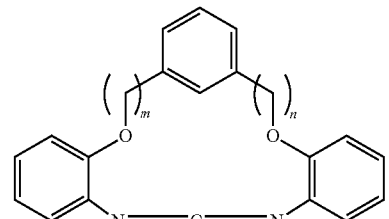

(m is an integer of 0 to 3, and n is an integer of 0 to 3)

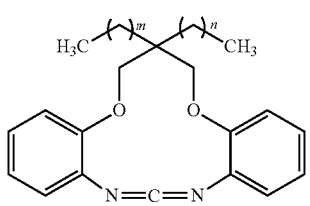

(m is an integer of 0 to 5, and n is an integer of 0 to 5)

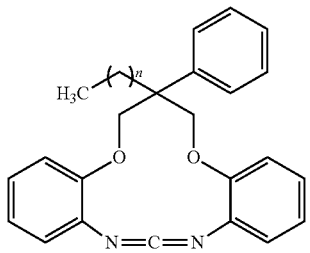

(n is an integer of 0 to 5)

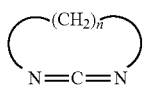

(n is an integer of 5 to 20)

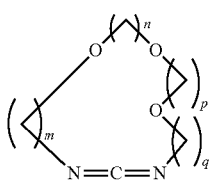

(m, n, p and q are each an integer of 1 to 6)

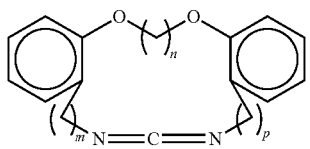

(m, n and p are each an integer of 1 to 6)

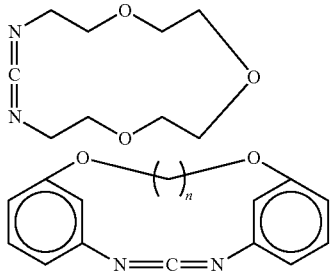

(n is an integer of 1 to 6)

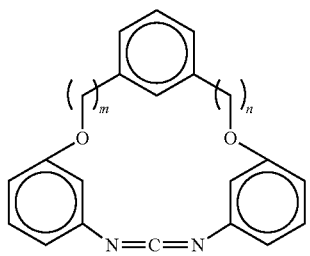

(m and n are each an integer of 0 to 3)

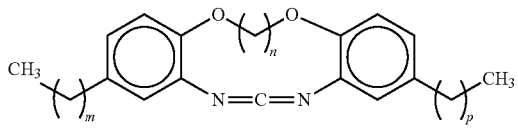

(m and p are each an integer of 1 to 5, and n is an integer of 1 to 6)

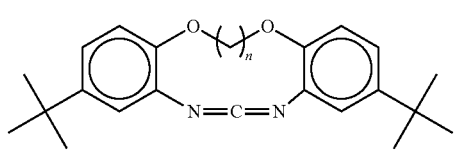

(n is an integer of 1 to 6)

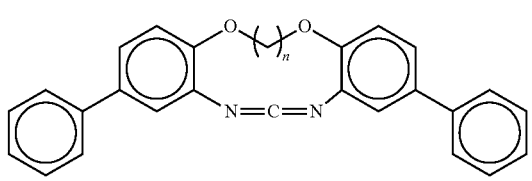

(n is an integer of 1 to 6)

<Cyclic Carbodiimide (b)>

Further, a compound represented by the following formula (3) (may be referred to as "cyclic carbodiimide (b)" hereinafter) can be given as the cyclic carbodiimide used in the present invention.

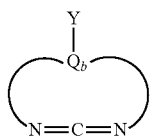

(3)

In the above formula, $Q_b$ is a tervalent bond group which is selected from an aliphatic group, an alicyclic group, an aromatic group or a combination of these and may contain a heteroatom or a substituent. Y is a carrier supporting the cyclic structure. The aliphatic group, alicyclic group and aromatic group are as defined in the formula (1). In the compound of the formula (3), one of the groups constituting $Q_b$ is tervalent.

$Q_b$ is preferably a tervalent bond group represented by the following formula (3-1), (3-2) or (3-3).

   (3-1)

   (3-2)

   (3-3)

In the above formulas, $Ar_b^1, Ar_b^2, R_b^1, R_b^2, X_b^1, X_b^2, X_b^3$, s and k are identical to $Ar^1, Ar^2, R^1, R^2, X^1, X^2, X^3$, s and k defined in the above formulas (1-1) to (1-3), respectively. However, one of them is a tervalent group.

Y is preferably a single bond, double bond, atom, atom group or polymer. Y is a bond part, and a plurality of cyclic structures are bonded together by Y to form a structure represented by the formula (3).

The following compounds are enumerated as examples of the cyclic carbodiimide compound (b).

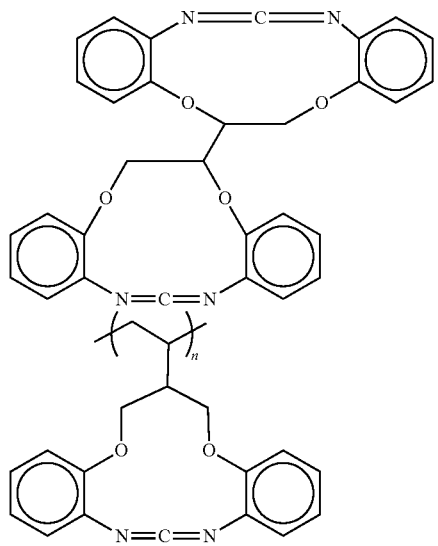

(n is a recurring unit)

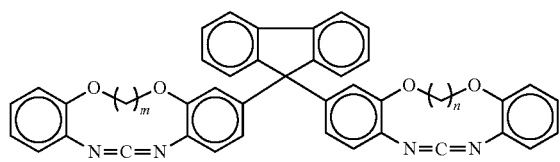

(m and n are each an integer of 1 to 6)

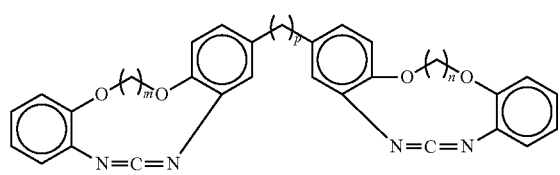

(p, m and n are each an integer of 1 to 6)

<Cyclic Carbodiimide (c)>

A compound represented by the following formula (4) (may be referred to as "cyclic carbodiimide (c)" hereinafter) can be given as the cyclic carbodiimide used in the present invention.

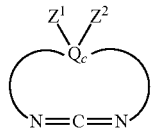   (4)

In the above formula, $Q_c$ is a tetravalent bond group which is selected from an aliphatic group, an alicyclic group, an aromatic group or a combination of these and may contain a heteroatom or a substituent. $Z^1$ and $Z^2$ are each a carrier supporting the cyclic structure. $Z^1$ and $Z^2$ may be bonded together to form a cyclic structure.

The aliphatic group, alicyclic group and aromatic group are as defined in the formula (1). In the compound of the formula (4), $Q_c$ is tetravalent. Therefore, one of these groups is tetravalent, or two of them are tervalent.

$Q_c$ is preferably a tetravalent bond group represented by the following formula (4-1), (4-2) or (4-3).

   (4-1)

   (4-2)

   (4-3)

$Ar_c^1, Ar_c^2, R_c^1, R_c^2, X_c^1, X_c^2, X_c^3$, s and k are identical to $Ar^1, Ar^2, R^1, R^2, X^1, X^2, X^3$, s and k defined in the above formulas (1-1) to (1-3), respectively. However, one of $Ar_c^1$, $Ar_c^2, R_c^1, R_c^2, X_c^1, X_c^2$ and $X_c^3$ is a tetravalent group, or two of them are tervalent groups.

$Z^1$ and $Z^2$ are each independently a single bond, double bond, atom, atom group or polymer. $Z^1$ and $Z^2$ are each a bond part, and a plurality of cyclic structures are bonded together by $Z^1$ and $Z^2$ to form a structure represented by the formula (4).

A compound represented by the following formula (4-1-1) is preferred as the cyclic carbodiimide compound (c).

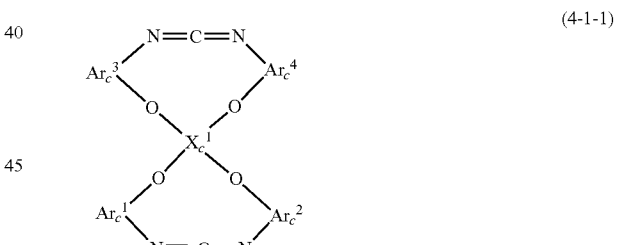   (4-1-1)

In the above formula, $X_c^1$ is an alkanetetrayl group having preferably 1 to 20 carbon atoms, more preferably 1 to 10 carbon atoms, much more preferably 1 to 6 carbon atoms. Examples of the alkanetetrayl group include isobutanetetrayl group, isopentanetetrayl group and neopentanetetrayl group. It is preferably a neopentanetetrayl group represented by the following formula.

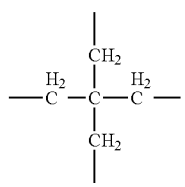

In the above formula, $Ar_c^1$, $Ar_c^2$, $Ar_c^3$ and $Ar_c^4$ are each independently an arylene group having 5 to 15 carbon atoms which may be substituted. Examples of the arylene group include phenylene group and naphthalenediyl group. The arylene group may be substituted. The substituent is an alkyl group having 1 to 20 carbon atoms, preferably 1 to 6 carbon atoms. Examples of the substituent include methyl group, ethyl group and propyl group.

A compound represented by the following formula (2-1-1c) is preferred as the cyclic carbodiimide (c).

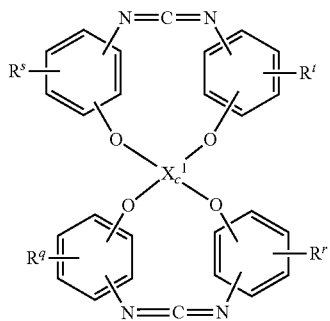

(2-1-1c)

In the above formula, $X_c^1$ is an alkanetetrayl group having preferably 1 to 20 carbon atoms, more preferably 1 to 10 carbon atoms, much more preferably 1 to 6 carbon atoms. Examples of the alkanetetrayl group include isobutanetetrayl group, isopentanetetrayl group and neopentanetetrayl group. It is preferably a neopentanetetrayl group represented by the following formula.

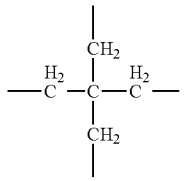

In the above formula, $R^q$, $R^r$, $R^s$ and $R^t$ are each independently an alkyl group having 1 to 20 carbon atoms, preferably 1 to 6 carbon atoms, or hydrogen atom. Examples of the alkyl group include methyl group, ethyl group and propyl group.

The following compounds can be given as examples of the cyclic carbodiimide compound (c).

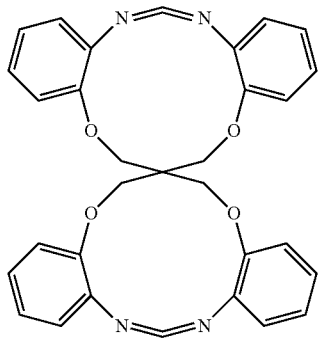

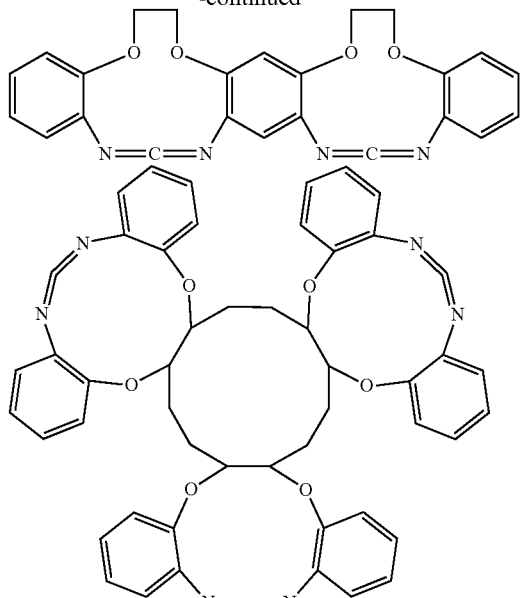

<Polymer>

In the present invention, the polymer for which the cyclic carbodiimide compound is used has an acid group. The acid group is at least one selected from the group consisting of carboxyl group, sulfonate group, sulfinate group, phosphonate group and phosphinate group. The melting point of the polymer is preferably 100° C. or higher, more preferably 150° C. or higher.

The polymer is at least one selected from the group consisting of polyester, polyamide, polyamide-imide, polyimide and polyester amide.

(Polyester)

The polyester is, for example, a polymer or copolymer obtained by polycondensing at least one selected from a dicarboxylic acid or ester forming compound thereof, a diol or ester forming compound thereof, a hydroxycarboxylic acid or ester forming compound thereof, and a lactone. It is preferably a thermoplastic polyester.

The thermoplastic polyester may contain a crosslinked structure treated with a radical generation source such as energy active line or an oxidizing agent to achieve moldability.

Examples of the above dicarboxylic acid or ester forming compound thereof include aromatic dicarboxylic acids such as terephthalic acid, isophthalic acid, phthalic acid, 2,6-naphthalenedicarboxylic acid, 1,5-naphthalenedicarboxylic acid, bis(p-carboxyphenyl)methane, anthracenedicarboxylic acid, 4,4'-diphenyl ether dicarboxylic acid, 5-tetrabutylphosphonium isophthalic acid and 5-sodium sulfoisophthalic acid. Aliphatic dicarboxylic acids such as oxalic acid, succinic acid, adipic acid, sebacic acid, azelaic acid, dodecanedioic acid, malonic acid, glutaric acid and dimeric acid are also included. Alicyclic dicarboxylic acids such as 1,3-cyclohexanedicarboxylic acid and 1,4-cyclohexanedicarboxylic acid are further included. Ester forming compounds thereof are still further included.

Examples of the above diol or ester forming compound thereof include aliphatic glycols having 2 to 20 carbon atoms such as ethylene glycol, 1,3-propanediol, propylene glycol, 1,4-butanediol, neopentyl glycol, 1,5-pentanediol, 1,6-hexanediol, decamethylene glycol, cyclohexanedimethanol, cyclohexanediol and dimer diol. Long-chain glycols having a molecular weight of 200 to 100,000, that is, polyethylene glycol, poly(1,3-propylene glycol), poly(1,2-propylene glycol) and polytetramethylene glycol are also included. Aromatic dioxy compounds, that is, 4,4'-dihydroxybiphenyl, hydroquinone, tert-butyl hydroquinone, bisphenol A, bisphenol S and bisphenol F are further included. Ester forming compounds thereof are still further included.

Examples of the above hydroxycarboxylic acid include glycolic acid, lactic acid, hydroxypropionic acid, hydroxybutyric acid, hydroxyvaleric acid, hydroxycaproic acid, hydroxybenzoic acid, p-hydroxybenzoic acid, 6-hydroxy-2-naphthoic acid and ester forming compounds thereof. Examples of the above lactone include caprolactone, valerolactone, propiolactone, undecalactone and 1,5-oxepan-2-one.

Aromatic polyesters obtained by polycondensing an aromatic dicarboxylic acid or ester forming compound thereof and an aliphatic diol or ester forming compound thereof as the main ingredients are enumerated as examples of the polyester. Examples of the aromatic carboxylic acid or ester forming compound thereof include terephthalic acid, naphthalene-2,6-dicarboxylic acid and ester forming compounds thereof. Examples of the aliphatic diol or ester forming compound thereof include ethylene glycol, propylene glycol and butanediol.

Preferred examples of the aromatic polyester include polyethylene terephthalate, polyethylene naphthalate, polytrimethylene terephthalate, polypropylene naphthalate, polybutylene terephthalate, polybutylene naphthalate, polyethylene (terephthalate/isophthalate), polytrimethylene (terephthalate/isophthalate), polybutylene (terephthalate/isophthalate), polyethylene terephthalate.polyethylene glycol, polytrimethylene terephthalate.polyethylene glycol, polybutylene terephthalate.polyethylene glycol, polybutylene naphthalate.polyethylene glycol, polyethylene terephthalate.poly(tetramethyleneoxide)glycol, polytrimethylene terephthalate.poly(tetramethyleneoxide)glycol, polybutylene terephthalate.poly(tetramethyleneoxide)glycol, polybutylene naphthalate.poly(tetramethyleneoxide)glycol, polyethylene (terephthalate/isophthalate).poly(tetramethyleneoxide)glycol, polytrimethylene(terephthalate/isophthalate).poly(tetramethyleneoxide)glycol, polybutylene (terephthalate/isophthalate).poly(tetramethyleneoxide)glycol, polybutylene (terephthalate/succinate), polyethylene(terephthalate/succinate), polybutylene (terephthalate/adipate) and polyethylene (terephthalate/adipate).

Aliphatic polyesters include polymers comprising an aliphatic hydroxycarboxylic acid as the main constituent component, polymers obtained by polycondensing an aliphatic polycarboxylic acid or ester forming compound thereof and an aliphatic polyhydric alcohol as the main ingredients, and copolymers thereof.

The polymers comprising an aliphatic hydroxycarboxylic acid as the main constituent component include polycondensates such as glycolic acid, lactic acid, hydroxypropionic acid, hydroxybutyric acid, hydroxyvaleric acid and hydroxycaproic acid, and copolymers thereof. Out of these, polyglycolic acid, polylactic acid, poly(3-hydroxycarbonbutyric acid), poly(4-polyhydroxybutyric acid), poly(3-hydroxhexanoic acid), polycaprolactone and copolymers thereof are preferred. Poly(L-lactic acid), poly(D-lactic acid), stereocomplex polylactic acid and racemic polylactic acid are particularly preferred.

Polymers comprising an aliphatic polycarboxylic acid and an aliphatic polyhydric alcohol as the main constituent components are also used as the aliphatic polyester. Examples of the polycarboxylic acid include aliphatic dicarboxylic acids such as oxalic acid, succinic acid, adipic acid, sebacic acid, azelaic acid, dodecanedioic acid, malonic acid, glutaric acid and dimeric acid, alicyclic dicarboxylic acid units such as 1,3-cyclohexanedicarboxylic acid and 1,4-cyclohexanedicarboxylic acid, and ester forming compounds thereof. Examples of the diol component include aliphatic glycols having 2 to 20 carbon atoms such as ethylene glycol, 1,3-propanediol, propylene glycol, 1,4-butanediol, neopentyl glycol, 1,5-pentanediol, 1,6-hexanediol, decamethylene glycol, cyclohexanedimethanol, cyclohexanediol and dimer diol. Long-chain glycols having a molecular weight of 200 to 100,000, that is, polyethylene glycol, poly(1,3-proylene glycol), poly(1,2-propylene glycol) and polytetramethylene glycol are also included. More specifically, polyethylene adipate, polyethylene succinate, polybutylene adipate, polybutylene succinate and copolymers thereof are included.

Further, wholly aromatic polyesters include polymers obtained by polycondensing an aromatic carboxylic acid or ester forming compound thereof, preferably terephthalic acid, naphthalene-2,6-dicarboxylic acid or ester forming compound thereof, and an aromatic polyhydroxy compound or ester forming compound thereof as the main ingredients.

More specifically, poly(4-oxyphenylene-2,2-propylidene-4-oxyphenylene-terephthaloyl-co-isophthaloyl) is such an example.

These polyesters contain 1 to 50 eq/ton of a terminal carboxyl group and/or a terminal hydroxyl group as a carbodiimide reactive component. Since these terminal groups, especially the carboxyl group reduces the stability of a polyester, it is preferably sealed with a cyclic carbodiimide compound.

When the terminal carboxyl group is sealed with a carbodiimide compound, it can be advantageously sealed without producing a toxic free isocyanate by using the cyclic carbodiimide compound of the present invention.

Further, as an additional effect, the increase or decrease of the molecular weight of a polyester by the chain extension function of a terminal isocyanate group which is formed in the polyester and not liberated when the terminal group is sealed with the cyclic carbodiimide compound and a terminal hydroxyl group or a terminal carboxyl group existent in the polyester can be suppressed more efficiently as compared with a conventional linear carbodiimide compound. This is of great industrial significance.

The above polyesters can be produced by known methods (for example, methods described in the saturated polyester resin handbook (written by Kazuo Yuki, published by Nikkan Kogyo Shimbun on Dec. 22, 1989).

Examples of the polyester further include unsaturated polyester resins obtained by copolymerizing an unsaturated polycarboxylic acid or ester forming compound thereof and polyester elastomers containing a low-melting polymer segment besides the above polyesters.

Examples of the unsaturated polycarboxylic acid include maleic anhydride, tetrahydromaleic anhydride, fumaric acid and endomethylene tetrahydromaleic anhydride. Monomers are added to the unsaturated polyester to control its curing properties, and the unsaturated polyester is cured by heat, radical, light, or active energy line such as electron beam and molded. The control of the carboxyl group in the unsaturated polyester is an important technical matter with respect to rheologic characteristics such as thixotropy and resin durability. Advantages that the carboxyl group can be sealed and controlled by the cyclic carbodiimide compound without producing a toxic free isocyanate and that the molecular weight of the unsaturated polyester can be increased effectively by the cyclic carbodiimide compound are of great industrial significance.

Further, in the present invention, the polyester may be a polyester elastomer obtained by copolymerizing a soft component. The polyester elastomer is a block copolymer comprising a high-melting polyester segment and a low-melting polymer segment having a molecular weight of 400 to 6,000 as described in publicly known documents, for example, JP-A 11-92636. The melting point of a polymer composed of a high-melting polyester segment alone is 150° C. or higher. The melting point or softening point of a polymer composed of a low-melting polymer segment alone which comprises an aliphatic polyester produced from a polyalkylene glycol or an aliphatic dicarboxylic acid having 2 to 12 carbon atoms and an aliphatic glycol having 2 to 10 carbon atoms is 80° C. or lower. Although the elastomer has a problem with hydrolytic stability, the significance of being able to control its carboxyl group by the cyclic carbodiimide compound and the industrial significance of being able to suppress the reduction of its molecular weight or increase its molecular weight without any safety problem by the cyclic carbodiimide compound are great.

The polyester preferably contains at least one selected from the group consisting of butylene terephthalate, ethylene terephthalate, trimethylene terephthalate, ethylene naphthalene dicarboxylate and butylene naphthalene dicarboxylate as the main recurring unit. The polymer is preferably an aliphatic polyester, particularly preferably polylactic acid.
(Polyamide)

The polyamide is a thermoplastic polymer having an amide bond obtained mainly from an amino acid, lactam or diamine and a dicarboxylic acid or amide forming compound thereof.

In the present invention, a polycondensate obtained by condensing a diamide and a dicarboxylic acid or acyl active form, a polymer obtained by polycondensing an aminocarboxylic acid or lactam, or an amino acid, or a copolymer thereof may be used as the polyamide. The diamine is selected from an aliphatic diamine and an aromatic diamine.

Examples of the aliphatic diamine include tetramethylenediamine, hexamethylenediamine, undecamethylenediamine, dodecamethylenediamine, 2,2,4-trimethylhexamethylenediamine, 2,4,4-trimethylhexamethylenediamine, 5-methylnonamethylenediamine, 2,4-dimethyloctamethylenediamine, metaxylylenediamine, paraxylylenediamine, 1,3-bis(aminomethyl)cyclohexane, 1-amino-3-aminomethyl-3,5,5-trimethylcyclohexane, 3,8-bis(aminomethyl)tricyclodecane, bis(4-aminocyclohexyl)methane, bis(3-methyl-4-aminocyclohexyl)methane, 2,2-bis(4-aminocyclohexyl)propane, bis(aminopropyl)piperazine and aminoethylpiperazine.

Examples of the aromatic diamine include p-phenylenediamine, m-phenylenediamine, 2,6-naphthalenediamine, 4,4'-diphenyldiamine, 3,4'-diphenyldiamine, 4,4'-diaminodiphenyl ether, 3,4'-diaminodiphenyl ether, 4,4'-diaminodiphenyl sulfone, 3,4'-diaminodiphenyl sulfone, 4,4'-diaminodiphenyl ketone, 3,4'-diaminodiphenyl ketone and 2,2-bis(4-aminophenyl)propane.

Examples of the dicarboxylic acid include adipic acid, suberic acid, azelaic acid, sebacic acid, dodecanoic acid, terephthalic acid, isophthalic acid, naphthalenedicarboxylic acid, 2-chloroterephthalic acid, 2-methylterephthalic acid, 5-methylisophthalic acid, 5-sodium sulfoisophthalic acid, hexahydroterephthalic acid, hexahydroisophthalic acid and diglycolic acid.

Specific examples of the polyamide include aliphatic polyamides such as polycapramide (nylon 6), polytetramethylene adipamide (nylon 46), polyhexamethylene adipamide (nylon 66), polyhexamethylene sebacamide (nylon 610), polyhexamethylene dodecamide (nylon 612), polyundecamethylene adipamide (nylon 116), polyundecaneamide (nylon 11) and polydodecaneamide (nylon 12).

Aliphatic-aromatic polyamides such as polytrimethyl hexamethylene terephthalamide, polyhexamethylene isophthalamide (nylon 6I), polyhexamethylene terephthal/isophthalamide (nylon 6T/6I), polybis(4-aminocyclohexyl)methane dodecamide (nylon PACM12), polybis(3-methyl-4-aminocyclohexyl)methane dodecamide (nylon dimethyl PACM12), polymetaxylylene adipamide (nylon MXD6), polyundecamethylene terephthalamide (nylon 11T), polyundecamethylene hexahydroterephthalamide (nylon 11T(H)) and copolyamides thereof, and copolymers and mixtures thereof are also included.

Poly(p-phenylene terephthalamide) and poly(p-phenylene terephthalamide-co-isophthalamide) are further included.

Examples of the amino acid include ω-aminocaproic acid, ω-aminoenanthic acid, ω-aminocaprylic acid, ω-aminopelargonic acid, ω-aminocapric acid, 11-aminoundecanoic acid, 12-aminododecanoic acid and paraaminomethylbenzoic acid, and examples of the lactam include ω-caprolactam, ω-enantholactam, ω-capryllactam and ω-laurolactam.

The molecular weights of these polyamides are not particularly limited but the relative viscosity measured at 25° C. of a 98% concentrated sulfuric acid solution containing 1 wt % of the polyamide is preferably 2.0 to 4.0.

These amide resins may be produced by well known methods, for example, methods described in the polyamide resin handbook (written by Osamu Fukumoto and published by Nikkan Kogyo Shimbun on Jan. 30, 1988).

Further, the polyamide includes a polyamide known as a polyamide elastomer. The polyamide is a graft or block copolymer obtained by reacting a polyamide forming component having 6 or more carbon atoms with a poly(alkyleneoxide)glycol. The bond between the polyamide forming component having 6 or more carbon atoms and the poly(alkyleneoxide)glycol component is generally an ester bond or an amide bond but not limited to these, and a third component such as dicarboxylic acid or diamine may be used as a reaction component for these components.

Examples of the poly(alkyleneoxide)glycol include polyethylene oxide glycol, poly(1,2-propyleneoxide)glycol, poly(1,3-propyleneoxide)glycol, poly(tetramethyleneoxide)glycol, poly(hexamethyleneoxide)glycol, block or random copolymer of ethylene oxide and propylene oxide, and block or random copolymer of ethylene oxide and tetrahydrofuran. The number average molecular weight of the poly(alkyleneoxide)glycol is preferably 200 to 6,000, more preferably 300 to 4,000 from the viewpoints of polymerizability and stiffness.

The polyamide elastomer used in the present invention is preferably a polyamide elastomer obtained by polymerizing caprolactam, polyethylene glycol and terephthalic acid.

Although the polyamide contains 30 to 100 eq/ton of a carboxyl group and 30 to 100 eq/ton of an amino group as easily understood from its raw materials, it is known that the carboxyl group has an unfavorable effect on the stability of the polyamide.

The significance of a composition whose carboxyl group content is reduced to not more than 20 eq/ton, preferably not more than 10 eq/ton, more preferably not more than that without a safety problem and whose molecular weight reduction is suppressed more effectively by the cyclic carbodiimide compound of the present invention is great.

(Polyamide-Imide)

The polyamide-imide used in the present invention has a main recurring structural unit represented by the following formula (I).

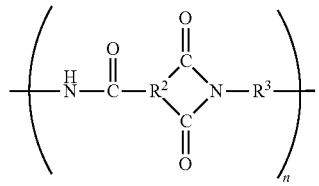

(In the above formula, $R^2$ is a tervalent organic group, $R^3$ is a divalent organic group, and n is a positive integer.)

Typical methods of synthesizing this polyamide-imide include (1) one in which a diisocyanate and a tribasic acid anhydride are reacted with each other, (2) one in which a diamine and a tribasic acid anhydride are reacted with each other, and (3) one in which a diamine and a tribasic acid anhydride chloride are reacted with each other. The method of synthesizing the polyamide-imide used in the present invention is not limited to these. Typical compounds used in the above synthesizing methods are listed below.

Preferred examples of the diisocyanate include 4,4'-diphenylmethane diisocyanate, xylylene diisocyanate, 3,3'-diphenylmethane diisocyanate, 4,4'-diphenyl ether diisocyanate, 3,3'-diphenyl ether diisocyanate and paraphenylene diisocyanate.

Preferred examples of the diamine include 4,4'-diaminodiphenylsulfone, 3,3'-diaminodiphenylsulfone, 4,4'-diaminodiphenyl ether, 3,3'-diaminodiphenyl ether, 4,4'-diaminodiphenyl methane, 3,3'-diaminodiphenyl methane, xylylenediamine and phenylenediamine.

Out of these, 4,4'-diphenylmethane diisocyanate, 3,3'-diphenylmethane diisocyanate, 4,4'-diphenyl ether diisocyanate, 3,3'-diphenyl ether diisocyanate, 4,4'-diaminodiphenyl ether, 3,3'-diaminodiphenyl ether, 4,4'-diaminodiphenyl methane and 3,3'-diaminodiphenyl methane are more preferred.

The tribasic acid anhydride is preferably trimellitic anhydride, and the tribasic acid anhydride chloride is preferably trimellitic anhydride chloride.

To synthesize the polyamide-imide, a dicarboxylic acid or a tetracarboxylic dianhydride can be reacted simultaneously as long as the characteristic properties of the polyamide-imide resin are not impaired. Examples of the dicarboxylic acid include terephthalic acid, isophthalic acid and adipic acid. Examples of the tetracarboxylic dianhydride include pyromellitic dianhydride, benzophenone tetracarboxylic dianhydride and biphenyl tetracarboxylic dianhydride. They are preferably used in an amount of not more than 50% by equivalent based on the total of all the acid components.

Since the durability of the polyamide-imide may be reduced by the concentration of the carboxyl group contained in the polymer, the concentration of the carboxyl group is preferably reduced to 1 to 10 eq/ton or below this range. In the cyclic carbodiimide compound of the present invention, the concentration of the carboxyl group can be advantageously reduced to the above range.

(Polyimide)

The polyimide is not particularly limited, and conventionally known polyimides may be used. Out of these, a thermoplastic polyimide is preferably selected. An example of the polyimide is the following polyimide comprising a diamine component and a tetracarboxylic acid.

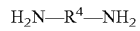

[in the above formula, $R^4$ is
(i) a single bond,
(ii) an aliphatic hydrocarbon group having 2 to 12 carbon atoms,
(iii) an alicyclic group having 4 to 30 carbon atoms,
(iv) an aromatic group having 6 to 30 carbon atoms,
(v) -Ph-O—$R^5$—O-Ph- ($R^5$ is a phenylene group or Ph-$W^1$-Ph-, $W^1$ is a single bond, alkylene group having 1 to 4 carbon atoms which may be substituted by a halogen atom, —O-Ph-O, —O—, —CO—, —S—, —SO— or —$SO_2$—), or
(vi) —$R^6$—$(SiR^7{}_2O)_m$—$SiR^7{}_2$—$R^6$— ($R^6$ is —$(CH_2)_s$—, —$(CH_2)_s$-Ph-, —$(CH_2)_s$—O-Ph- or Ph-, m is an integer of 1 to 100, s is an integer of 1 to 4, and $R^7$ is an alkyl group having 1 to 6 carbon atoms, phenyl group or alkylphenyl group having 1 to 6 carbon atoms).]

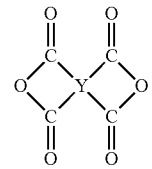

[In the above formula, Y is a tetravalent aliphatic group having 2 to 12 carbon atoms, a tetravalent alicyclic group having 4 to 8 carbon atoms, a tetravalent aromatic group of a mono- or poly-condensed ring having 6 to 14 carbon atoms, or >Ph-$W^2$-Ph< ($W^2$ is a single bond, an alkylene group having 1 to 4 carbon atoms which may be substituted by a halogen atom, —O-Ph-O—, —O—, —CO—, —SO— or —$SO_2$—).]

Examples of the tetracarboxylic anhydride used in the production of the polyimide include pyromellitic anhydride (PMDA), 4,4'-oxydiphthalic anhydride (ODPA), biphenyl-3,3',4,4'-tetracarboxylic anhydride (BPDA), benzophenone-3,3',4,4'-tetracarboxylic anhydride (BTDA), ethylene tetracarboxylic anhydride, butane tetracarboxylic anhydride, cyclopentane tetracarboxylic anhydride, benzophenone-2,2',3,3'-tetracarboxylic anhydride, biphenyl-2,2',3,3'-tetracarboxylic anhydride, anhydrous 2,2-bis(3,4-dicarboxyphenyl)propane, anhydrous 2,2-bis(2,3-dicarboxyphenyl)propane, anhydrous bis(3,4-dicarboxyphenyl)ether, anhydrous bis(3,4-dicarboxyphenyl)sulfone, anhydrous 1,1-bis(2,3-dicarboxyphenyl)ethane, anhydrous bis(2,3-dicarboxyphenyl)methane, anhydrous bis(3,4-dicarboxyphenyl)methane, 4,4'-(p-phenylenedioxy)diphthalic anhydride, 4,4'-(m-phenylenedioxy)diphthalic anhydride, naphthalene-2,3,6,7-tetracarboxylic anhydride, naphthalene-1,4,5,8-tetracarboxylic anhydride, naphthalene-1,2,5,6-tetracarboxylic anhydride, benzene-1,2,3,4-tetracarboxylic anhydride, perylene-3,4,9,10-tetracarboxylic anhydride, anthracene-2,3,6,7-tetracarboxylic anhydride and phenanthrene-1,2,7,8-tetracarboxylic anhydride. The present invention is not limited to these. These dicarboxylic anhydrides may be used alone or in combination of two or more. Out of these, pyromellitic anhydride (PMDA), 4,4'-oxydiphthalic anhydride (ODPA), biphenyl-3,3',4,4'-tetracarboxylic anhydride (BPDA), benzophenone-3,3',4,4'-tetracarboxylic anhydride and biphenylsulfone-3,3',4,4'-tetracarboxylic anhydride (DSDA) are preferably used.

In the present invention, examples of the diamine used in the production of the polyimide include 4,4'-diaminodiphenyl ether, 4,4'-diaminodiphenylmethane, 4,4'-diaminodiphenylsulfone, 4,4'-diaminodiphenyl thioether, 4,4'-di(meta-aminophenoxy)diphenylsulfone, 4,4'-di(para-aminophenoxy)diphenylsulfone, o-phenylenediamine, m-phenylenediamine, p-phenylenediamine, benzidine, 2,2'-diaminobenzophenone, 4,4'-diaminobenzophenone, 4,4'-diaminodiphenyl-2,2'-propane, 1,5-diaminonaphthalene, 1,8-diaminonaphthalene, trimethylenediamine, tetramethylenediamine, hexamethylenediamine, 4,4-dimethylheptamethylenediamine, 2,11-dodecadiamine, di(para-aminophenoxy)dimethylsilane, 1,4-di(3-aminopropyl-diaminosilane)benzene, 1,4-diaminocyclohexane, ortho-tolyldiamine, meta-tolyldiamine, acetoguanamine, benzoguanamine, 1,3-bis(3-aminophenoxy)benzene (APB), bis[4-(3-aminophenoxy)phenyl]methane, 1,1-bis[4-(3-aminophenoxy)phenyl]ethane, 1,2-bis[4-(3-aminophenoxy)phenyl]ethane, 2,2-bis[4-(3-aminophenoxy)phenyl]ethane, 2,2-bis[4-(3-aminophenoxy)phenyl]propane, 2,2-bis[4-(3-aminophenoxy)phenyl]butane, 2,2-bis[4-(3-aminophenoxy)phenyl]-1,1,1,3,3,3-hexafluoropropane, 4,4'-di(3-aminophenoxy)biphenyl, di[4-(3-aminophenoxy)phenyl]ketone, di[4-(3-aminophenoxy)phenyl]sulfide, di[4-(3-aminophenoxy)phenyl]sulfoxide, di[4-(3-aminophenoxy)phenyl]sulfone and di(4-(3-amionohpenoxy)phenyl)ether. The present invention is not limited to these. The above diamines may be used alone or in combination.

Examples of the thermoplastic polyimide include polyimides comprising a tetracarboxylic anhydride and a known diamine such as p-phenylenediamine, cyclohexanediamine or hydrogenated bisphenol A type diamine and represented by the following formulas, and Ultem1000, Ultem1010, UltemCRS5001 and UltemXH6050 commercially available from General Electric Co., Ltd. and Auram 250AM from Mitsui Chemical Co., Ltd.

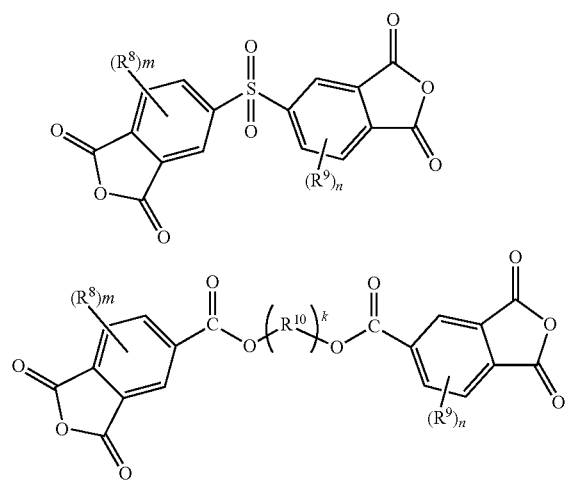

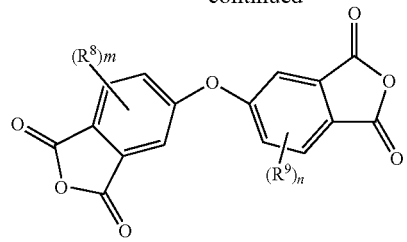

[In the above formulas, $R^8$ and $R^9$ are each independently a hydrogen atom, a linear or branched alkyl group having 1 to 10 carbon atoms, or an aryl group, $R^{10}$ is an arylene group having 6 to 30 carbon atoms or an alkylene group having 2 to 20 carbon atoms, m and n are each an integer of 0 to 5, and k is an integer of 1 to 3.]

(Polyester Amide)

Examples of the polyester amide include conventionally known polyester amides obtained by copolymerizing a polyester component and a polyamide component. Out of these, a thermoplastic polyester amide is preferably selected.

The polyester amide can be synthesized by known methods. For example, the above polyamide component is first subjected to a polycondensation reaction so as to synthesize a polyamide having a terminal functional group and then the polyester component is polymerized in the presence of the polyamide. This polycondensation reaction is generally realized by carrying out an amidation reaction as a first stage and an esterification reaction as a second stage.

The above polyester components are preferably selected as the polyester component. The above polyamide components are preferably selected as the polyamide component.

Any known additives and fillers can be added to these polymers on which the cyclic carbodiimide is caused to act as long as their effects are not lost when they react with the carbodiimide. The additives include an antioxidant, heat stabilizer, lubricant, nucleating agent, optical stabilizer, antistatic agent and coloring material. The fillers include glass flakes, glass fibers, organic fibers, talc and inorganic fillers.

<Method of Using a Carbodiimide Compound>

The sealing of an acid group contained in a polymer can be carried out by mixing together the cyclic carbodiimide compound and the polymer to react the cyclic carbodiimide compound with the acid group. The cyclic carbodiimide compound can be added to the polymer as a solution, a melt or a master batch of a polymer for which it is used. Or, a solid polymer is brought into contact with a liquid containing the cyclic carbodiimide compound dissolved therein, dispersed therein or molten therein to be impregnated with the cyclic carbodiimide compound.

In the case of the method in which the cyclic carbodiimide compound is added as a solution, a melt or a master batch of a polymer, a conventionally known kneader is used to add the cyclic carbodiimide compound. For kneading, the cyclic carbodiimide compound is preferably kneaded in a solution state or a molten state from the viewpoint of uniform kneading. The kneader is not particularly limited, and conventionally known vertical reactors, mixing tanks, kneading tanks or single-screw or multi-screw horizontal kneaders may be used. For example, a single-screw or multi-screw extruder or kneader is used.

The time during which the cyclic carbodiimide compound is mixed with the polymer differs according to the mixer and the mixing temperature but preferably 0.1 minute to 2 hours, more preferably 0.2 to 60 minutes, much more preferably 0.2 to 30 minutes.

As the solvent may be used a solvent which is inert to the polymer and the cyclic carbodiimide compound. A solvent which has affinity for both of them and dissolves at least part of each of them is preferred. The solvent is selected from a hydrocarbon-based solvent, a ketone-based solvent, an ester-based solvent, an ether-based solvent, a halogen-based solvent and an amide-based solvent.

Examples of the hydrocarbon-based solvent include hexane, cyclohexane, benzene, toluene, xylene, heptane and decane. Examples of the ketone-based solvent include acetone, methyl ethyl ketone, diethyl ketone, cyclohexanone and isophorone. Examples of the ester-based solvent include ethyl acetate, methyl acetate, ethyl succinate, methyl carbonate, ethyl benzoate and diethylene glycol diacetate. Examples of the ether-based solvent include diethyl ether, dibutyl ether, tetrahydrofuran, dioxane, diethylene glycol dimethyl ether, triethylene glycol diethyl ether and diphenyl ether.

Examples of the halogen-based solvent include dichloromethane, chloroform, tetrachloromethane, dichloroethane, 1,1',2,2'-tetrachloroethane, chlorobenzene and dichlorobenzene. Examples of the amide-based solvent include formamide, N,N-dimethylformamide, N,N-dimethylacetamide and N-methyl-2-pyrrolidone. These solvents may be used alone or as a mixture.

In the present invention, the solvent is used in an amount of 1 to 1,000 parts by weight based on 100 parts by weight of the total of the polymer and the cyclic carbodiimide compound. When the amount of the solvent is smaller than 1 part by weight, there is no point in using the solvent. Although there is no upper limit to the amount of the solvent, it is about 1,000 parts by weight from the viewpoints of manipulation ease and reaction efficiency.

In the case of the method in which the solid polymer is brought into contact with a liquid containing the cyclic carbodiimide compound dissolved therein, dispersed therein or molten therein to be impregnated with the cyclic carbodiimide compound, the solid polymer is brought into contact with the carbodiimide dissolved in the above solvent, or the solid polymer is brought into contact with an emulsion of the carbodiimide. To bring the solid polymer into contact with the cyclic carbodiimide compound, the polymer is immersed in the cyclic carbodiimide compound, or coated or sprayed with the cyclic carbodiimide compound.

A sealing reaction by the cyclic carbodiimide compound of the present invention can be carried out at room temperature (25° C.) to 300° C. However, the reaction temperature is preferably 50 to 280° C., more preferably 100 to 280° C. from the viewpoint of reaction efficiency. Although the reaction proceeds more at a temperature at which the polymer is molten, the reaction is preferably carried out at a temperature lower than 300° C. to suppress the sublimation and decomposition of the cyclic carbodiimide compound. To reduce the melting temperature and increase the agitation efficiency of the polymer, use of the solvent is effective.

Although the reaction proceeds fully swiftly without a catalyst, a catalyst for promoting the reaction may be used. As the catalyst may be used a catalyst which is used for a conventional linear carbodiimide compound (Patent Document 2: JP-A 2005-2174). Examples of the catalyst include alkali metal compounds, alkali earth metal compounds, tertiary amine compounds, imidazole compounds, quaternary ammonium salts, phosphine compounds, phosphonium salts, phosphoric acid esters, organic acids and Lewis acid. They may be used alone or in combination of two or more. The amount of the catalyst which is not particularly limited is preferably 0.001 to 1 part by weight, more preferably 0.01 to 0.1 part by weight, much more preferably 0.02 to 0.1 part by weight based on 100 parts by weight of the total of the polymer and the cyclic carbodiimide compound.

As for the amount of the cyclic carbodiimide compound, the content of the carbodiimide group in the cyclic carbodiimide compound is selected from a range from 0.5 to 100 equivalents based on 1 equivalent of the acid group. When the content of the carbodiimide group is lower than 0.5 equivalent, there may be no point in using the carbodiimide. When the content is higher than 100 equivalents, the characteristic properties of a matrix may change. From this viewpoint of view, the content of the carbodiimide group is preferably 0.6 to 75 equivalents, more preferably 0.65 to 50 equivalents, much more preferably 0.7 to 30 equivalents, particularly preferably 0.7 to 20 equivalents based on the above standard.

<Production Process of Cyclic Carbodiimide Compound>

As the process for producing the cyclic carbodiimide compound, a process for producing the compound from an amine compound through an isocyanate compound, a process for producing the compound from an amine compound through an isothiocyanate compound, a process for producing the compound from an amine compound through a triphenylphosphine compound, a process for producing the compound from an amine compound through an urea compound, a process for producing the compound from an amine compound through a thiourea compound, a process for producing the compound from a carboxylate compound through an isocyanate compound and a process for producing the compound by deriving a lactam compound may be employed.

(Production of Monocyclic Carbodiimide Compound (f))

The monocyclic carbodiimide compound (f) represented by the following formula (2-1-1) can be produced through the following steps (1) to (4).

(2-1-1)

(In the above formula, $Ar_a^1$ and $Ar_a^2$ are each independently an arylene group having 5 to 15 carbon atoms which may be substituted, and $X_a^1$ is an alkylene group having 1 to 20 carbon atoms.)

The step (1) is to obtain a nitro compound (c). The step (1) has step (1a) and step (1b). The step (2) is to obtain an amide compound (d) from the nitro compound (c). The step (3) and the step (4) are to obtain the monocyclic carbodiimide compound (f) from the amide compound (d). The step (3) to (4) has the embodiment of step (3a) through step (4a), and step (3b) through step (4b).

Stated more specifically, the carbodiimide compound (f) can be produced through the following schemes.
(scheme 1) step (1a)-step (2a)-step (3a)-step (4a)
(scheme 2) step (1a)-step (2a)-step (3b)-step (4b)
(scheme 3) step (1b)-step (2a)-step (3b)-step (4b)
(scheme 4) step (1b)-step (2a)-step (3a)-step (4a)
(Step (1a))

The step (1a) is to obtain the nitro compound (c) of the following formula by reacting a compound of the following formula (a-1), a compound of the following formula (a-2) and a compound of the following formula (b-1).

 (a-1)

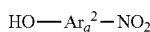 (a-2)

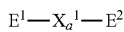 (b-1)

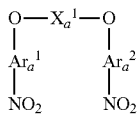 (c)

In the above formulas, $X_a^1$, $Ar_a^1$ and $Ar_a^2$ are as defined in the above formula (2-1-1).

$E^1$ and $E^2$ are each independently a group selected from the group consisting of halogen atom, toluenesulfonyloxy group, methanesulfonyloxy group, benzenesulfonyloxy group and p-bromobenzenesulfonyloxy group. Examples of the halogen atom include chlorine atom, bromine atom and iodine atom.

A conventionally known ether synthesizing method may be used for the reaction. For example, a Williamson's reaction in which a compound of the formula (a-1), a compound of the formula (a-2) and a compound of the formula (b-1) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds swiftly under the above conditions, a phase-transfer catalyst may be added to promote the reaction.

(Step (1b))

The step (1b) is to obtain the nitro compound of the following formula (c) by reacting a compound of the following formula (a-i), a compound of the following formula (a-ii) and a compound of the following formula (b-i).

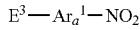 (a-i)

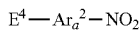 (a-ii)

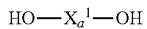 (b-i)

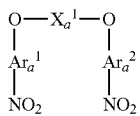 (c)

In the above formulas, $Ar_a^1$, $Ar_a^2$ and $X_a^1$ are as defined in the above formula (2-1-1). $E^3$ and $E^4$ are each independently a group selected from the group consisting of halogen atom, toluenesulfonyloxy group, methanesulfonyloxy group, benzenesulfonyloxy group and p-bromobenzenesulfonyloxy group.

A conventionally known ether synthesizing method may be used for the reaction. For example, a Williamson's reaction in which a compound of the formula (a-i), a compound of the formula (a-ii) and a compound of the formula (b-i) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds under the above conditions, a phase-transfer catalyst may be added to promote the reaction. A tetrabutylammonium salt, trioctylmethylammonium salt, benzyldimethyloctadecylammonium salt or crown ether is used as the phase-transfer catalyst.

(Step (2))

The step (2) is to obtain the amine compound (d) of the following formula by reducing the obtained nitro compound (c).

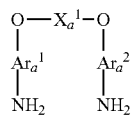 (d)

$Ar_a^1$, $Ar_a^2$ and $X_a^1$ are as defined in the above formula (2-1-1).

A conventionally known method may be used for the reaction. For example, the nitro compound (c) is catalytic reduced in a solvent in the presence of hydrogen and a catalyst.

Palladium carbon, palladium carbon-ethylenediamine complex, palladium-fibroin, palladium-polyethyleneimine, nickel or copper is used as the catalyst. Methanol, ethanol, isopropyl alcohol, dioxane, tetrahydrofuran, ethyl acetate, dichloromethane, chloroform or N,N-dimethylformamide is used as the solvent. The reaction temperature is preferably 25 to 100° C. Although the reaction proceeds at normal pressure, pressure is preferably applied to promote the reaction.

As another reaction for obtaining the amine compound (d), the nitro compound (c) is reacted with an acid and a metal, or the nitro compound (c) is reacted with hydrazine and a catalyst.

(Step (3a))

The step (3a) is to obtain a triphenylphosphine compound (e-1) of the following formula by reacting the obtained amine compound (d) with triphenylphosphine dibromide.

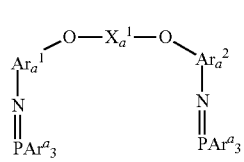 (e-1)

In the above formula, $Ar_a^1$, $Ar_a^2$ and $X_a^1$ are as defined in the above formula (2-1-1). $Ar^a$ is a phenyl group.

A conventionally known method may be used for the reaction. For example, the amine compound of the formula (d) is reacted with triphenylphosphine dibromide in a solvent in the presence of a basic compound. Triethylamine or pyridine is used as the basic compound. Dichloroethane, chloroform or benzene is used as the solvent. The reaction temperature is preferably 0 to 80° C.

(Step (4a))

The step (4a) is to obtain the cyclic carbodiimide compound (f) of the following formula by isocyanating the obtained triphenylphosphine compound in a reaction system and then decarbonating the isocyanated product directly.

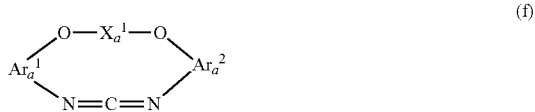
(f)

(In the above formula, $Ar_a^1$, $Ar_a^2$ and $X_a^1$ are as defined in the above formula (2-1-1).)

A conventionally known method may be used for the reaction. For example, the triphenylphosphine compound of the formula (e-1) is reacted in a solvent in the presence of di-tert-butyl dicarbonate and N,N-dimethyl-4-aminopyridine. Dichloromethane or chloroform is used as the solvent. The reaction temperature is preferably 10 to 40° C.

(Step (3b))

The step (3b) is to obtain an urea compound or thiourea compound of the following formula (e-2) by reacting the amine compound (d) with carbon dioxide or carbon disulfide.

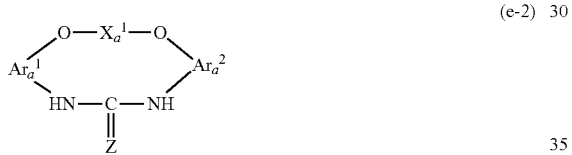
(e-2)

In the above formula, $Ar_a^1$, $Ar_a^2$ and $X_a^1$ are as defined in the above formula (2-1-1), and Z is an oxygen atom or sulfur atom.

A conventionally known method may be used for the reaction for obtaining the urea compound (e-2). For example, the amine compound (d) is reacted in a solvent in the presence of carbon dioxide, a phosphorus compound and a basic compound.

A phosphorous acid ester or a phosphonic acid ester is used as the phosphorus compound. Triethylamine, pyridine, imidazole or picoline is used as the basic compound. Pyridine, N,N-dimethylformamide, acetonitrile, chlorobenzene or toluene is used as the solvent. The reaction temperature is preferably 0 to 80° C.

As another reaction for obtaining the urea compound (e-2), the amine compound (d) is reacted with carbon monoxide, or the amine compound (d) is reacted with phosgene.

A conventionally known method may be used for the reaction for obtaining the thiourea compound (e-2). For example, the amine compound (d) is reacted in a solvent in the presence of carbon disulfide and a basic compound.

Triethylamine, pyridine, imidazole or picoline is used as the basic compound. Acetone, methanol, ethanol, isopropyl alcohol, 2-butanone, pyridine, N,N-dimethylformamide or acetonitrile is used as the solvent. The reaction temperature is preferably 25 to 90° C. Although the reaction proceeds swiftly under the above conditions, carbon tetrabromide may be used to promote the reaction.

(Step (4b))

The step (4b) is to obtain the cyclic carbodiimide compound (f) by dehydrating the obtained urea compound (e-2) or desulfurizing the thiourea compound (e-2).

A conventionally known method may be used for the reaction. For example, the urea compound or thiourea compound (e-2) is reacted in a solvent in the presence of toluenesulfonyl chloride or methylsulfonyl chloride to dehydrate the urea compound (e-2) or desulfurize the thiourea compound (e-2).

Dichloromethane, chloroform or pyridine is used as the solvent. The reaction temperature is preferably 0 to 80° C.

As another reaction for obtaining the cyclic carbodiimide compound (f), the urea compound (e-2) is reacted with mercury oxide, or the thiourea compound (e-2) is reacted with sodium hypochlorite.

<Production of Bicyclic Carbodiimide Compound (F)>

The bicyclic carbodiimide compound (F) represented by the following formula (4-1-1) can be produced through the following steps (1) to (4).

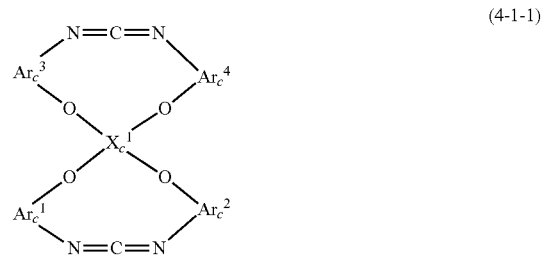
(4-1-1)

In the above formula, $X_c^1$ is an alkanetetrayl group having 1 to 20 carbon atoms. $Ar_c^1$, $Ar_c^2$, $Ar_c^3$ and $Ar_c^4$ are each independently an arylene group having 5 to 15 carbon atoms which may be substituted.

The step (1) is to obtain a nitro compound (C). The step (1) has step (1A) and step (1B). The step (2) is to obtain an amide compound (D) from the nitro compound (C). The step (3) and the step (4) are to obtain the bicyclic carbodiimide compound (F) from the amide compound (D). The step (3) to (4) has the embodiment of step (3A) through step (4A), and step (3B) through step (4B).

The carbodiimide compound (F) can be produced through the following schemes.

(scheme 1) step (1A)-step (2A)-step (3A)-step (4A)
(scheme 2) step (1A)-step (2A)-step (3B)-step (4B)
(scheme 3) step (1B)-step (2A)-step (3B)-step (4B)
(scheme 4) step (1B)-step (2A)-step (3A)-step (4A)

(Step (1A))

The step (1A) is to obtain a nitro compound of the following formula (C) by reacting compounds of the following formulas (A-1) to (A-4) and a compound of the following formula (B-1).

$$HO-Ar_c^1-NO_2 \quad (A-1)$$

$$HO-Ar_c^2-NO_2 \quad (A-2)$$

$$HO-Ar_c^3-NO_2 \quad (A-3)$$

$$HO-Ar_c^4-NO_2 \quad (A-4)$$

-continued

($X_c^1$ is

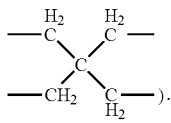

).

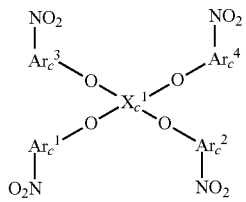
(C)

In the above formulas, $Ar_c^1$ to $Ar_c^4$ and $X_c^1$ are as defined in the formula (4-1-1). $E^1$ to $E^4$ are each independently a group selected from the group consisting of halogen atom, toluenesulfonyloxy group, methanesulfonyloxy group, benzenesulfonyloxy group and p-bromobenzenesulfonyloxy group.

The reaction conditions are the same as those in the above step (1a).

(Step (1B))

The step (1B) is to obtain the nitro compound of the following formula (C) by reacting compounds of the following formulas (A-i) to (A-iv) and a compound of the following formula (B-i).

 (A-i)

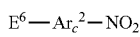 (A-ii)

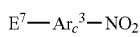 (A-iii)

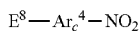 (A-iv)

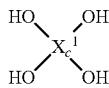 (B-i)

($X_c^1$ is

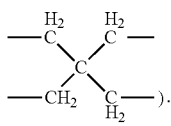

).

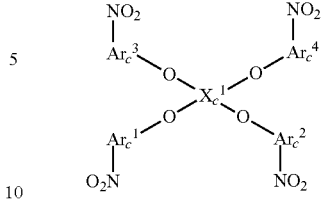
(B-1)

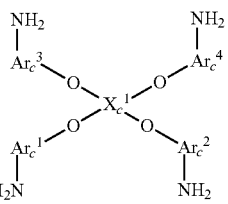
(C)

In the above formulas, $Ar_c^1$ to $Ar_c^4$ and $X_c^1$ are as defined in the formula (4-1-1). $E^5$ to $E^8$ are each independently a group selected from the group consisting of halogen atom, toluenesulfonyloxy group, methanesulfonyloxy group, benzenesulfonyloxy group and p-bromobenzenesulfonyloxy group.

The reaction conditions are the same as those in the above step (1b).

(Step (2A))

The step (2A) is to obtain the amine compound (D) of the following formula by reducing the obtained nitro compound.

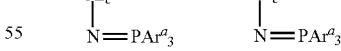
(D)

$Ar_c^1$ to $Ar_c^4$ and $X_c^1$ are as defined in the formula (4-1-1). The reaction conditions are the same as those in the above step (2a).

(Step (3A))

The step (3A) is to obtain a triphenylphosphine compound (E-1) of the following formula by reacting the obtained amine compound (D) with triphenylphosphine dibromide.

(E-1)

In the above formula, $Ar_c^1$ to $Ar_c^4$ and $X_c^1$ are as defined in the formula (4-1-1), and $Ar^a$ is a phenyl group. The reaction conditions are the same as those in the above step (3a).

(Step (4A))

The step (4A) is to obtain the compound (F) of the following formula by isocyanating the obtained triphenylphosphine compound in a reaction system and then decarbonating the isocyanated product directly.

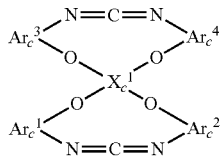

(F)

(In the above formula, $Ar_c^1$ to $Ar_c^4$ and $X_c^1$ are as defined in the formula (4-1-1).)

The reaction conditions are the same as those in the above step (4a).

(Step (3B))

The step (3B) is to obtain an urea compound or thiourea compound (E-2) of the following formula by reacting the amine compound with carbon dioxide or carbon disulfide.

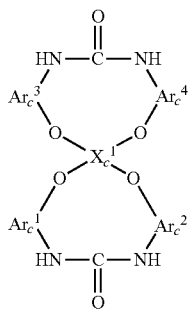

(E-2)

In the above formula, $Ar_c^1$ to $Ar_c^4$ and $X_c^1$ are as defined in the formula (4-1-1), and Z is an oxygen atom or sulfur atom. The reaction conditions are the same as those in the above step (3b).

(Step (4B))

The step (4B) is to obtain the compound (F) of the following formula by dehydrating the obtained urea compound or desulfurizing the thiourea compound.

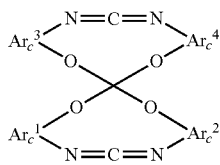

(F)

(In the above formula, $Ar_c^1$ to $Ar_c^4$ and $X_c^1$ are as defined in the formula (4-1-1).)

The reaction conditions are the same as those in the above step (4b).

Although the cyclic carbodiimide compound can seal the acid group of a polymer effectively, a conventionally known sealing agent for the carboxyl group of a polymer may be optionally used in combination as long as it does not work against the subject matter of the present invention. As the conventionally known carboxyl group sealing agent, agents disclosed by JP-A 2005-2174 such as epoxy compounds, oxazoline compounds and oxazine compounds may be used.

EXAMPLES

The following examples are provided to further illustrate the present invention.

Characteristic properties were measured by the following methods.

(1) Identification of Cyclic Carbodiimide Structure by NMR

The synthesized cyclic carbodiimide compound was confirmed by $^1$H-NMR and $^{13}$C-NMR. The JNR-EX270 of JEOL Ltd. was used for NMR. Heavy chloroform was used as the solvent.

(2) Identification of Carbodiimide Skeleton of Cyclic Carbodiimide by IR

The existence of the carbodiimide skeleton of the synthesized cyclic carbodiimide compound at 2,100 to 2,200 cm$^{-1}$ which is the characteristic of a carbodiimide was confirmed by FT-IR. The Magna-750 of Thermonicoley Co., Ltd. was used for FT-IR.

(3) Concentration of Carboxyl Group

The sample was dissolved in purified o-cresol in a nitrogen stream and titrated with an ethanol solution of 0.05 N potassium hydroxide by using Bromocresol Blue as an indicator.

Synthesis Example 1 Cyclic Carbodiimide CC1

CC1: MW=194

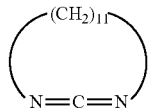

ω-laurinlactam (0.05 mol), trimethyloxonium fluoroborate (0.1 mol) and 100 ml of dichloromethane were fed to a reactor equipped with a stirrer and a heater in an N$_2$ atmosphere and reacted under reflux in the N$_2$ atmosphere. 6 hours after the reaction, the produced salt was removed by filtration, and the filtrate was washed with 100 ml of a 15% potassium carbonate aqueous solution 3 times and further with 100 ml of distilled water 3 times. An organic layer was dehydrated with 5 g of sodium sulfate and dichloromethane was removed under reduced pressure to obtain an intermediate product A.

Then, the intermediate product A (0.1 mol), hydroxylamine hydrochloride (0.11 mol), sodium hydrogen carbonate (0.15 mol) and 100 ml of methanol were fed to a reactor equipped with a stirrer and a heater in an N$_2$ atmosphere and reacted under reflux in the N$_2$ atmosphere. 6 hours after the reaction, the reaction mixture was filtered, and an intermediate product B was obtained from the filtrate by recrystallization.

Then, the intermediate product B (0.1 mol) and 50 ml of pyridine were fed to a reactor having a stirrer, a dropping funnel and an ice bath in an N$_2$ atmosphere and stirred. Methanesulfonyl chloride (0.11 mol) was gradually added dropwise to the resulting mixture. After the end of addition, a reaction was carried out in the ice bath in the N$_2$ atmosphere for 6 hours. When the reaction solution was transferred to a beaker containing 500 ml of water after the reaction, a light yellow solid separated out. The solid was collected by filtration and washed in 100 ml of water several times to obtain an intermediate product C.

Thereafter, the intermediate product C (0.1 mol) and 50 ml of dimethoxyethane were fed to a reactor equipped with a stirrer and an ice bath, and 20 ml of dimethoxyethane containing potassium tert-butoxide (0.11 mol) dispersed therein was gradually added to the resulting mixture in an N$_2$ atmosphere. After a reaction was carried out in the ice bath for 2 hours, CC1 was obtained from the reaction solution. The structure of CC1 was confirmed by NMR and IR.

Synthesis Example 2 Cyclic Carbodiimide CC2

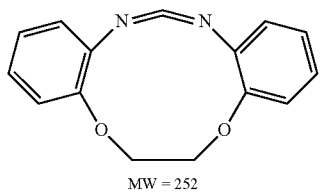 [SMILES: C1=Nc2ccccc2OCCOc2ccccc2N=1]

MW = 252 o-nitrophenol (0.11 mol), 1,2-dibromoethane (0.05 mol), potassium carbonate (0.33 mol) and 200 ml of N,N-dimethylformamide were fed to a reactor equipped with a stirrer and a heater in an $N_2$ atmosphere and reacted at 130° C. for 12 hours, DMF was removed under reduced pressure, the obtained solid was dissolved in 200 ml of dicloromethane, and the resulting solution was separated with 100 ml of water 3 times. An organic layer was dehydrated with 5 g of sodium sulfate and dichloromethane was removed under reduced pressure to obtain an intermediate product D (nitro compound).

Then, the intermediate product D (0.1 mol), 5% palladium carbon (Pd/C) (1 g) and 200 ml of ethanol/dichloromethane (70/30) were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected and the mixed solvent was removed, an intermediate product E (amine compound) was obtained.

Then, triphenylphosphine dibromide (0.11 mol) and 150 ml of 1,2-dichloroethane were fed to a reactor equipped with a stirrer, a heater and a dropping funnel in an $N_2$ atmosphere and stirred. A solution obtained by dissolving the intermediate product E (0.05 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product F (triphenylphosphine compound).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product F (0.05 mol) dissolved therein was gradually added dropwise to the resulting mixture at 25° C.

After the end of addition, a reaction was carried out for 12 hours. Thereafter, a solid obtained by removing dichloromethane was purified to obtain CC2. The structure of CC2 was checked by NMR and IR.

Example 1

End-Sealing of Polylactic Acid by CC2

0.005 part by weight of tin octylate was added to 100 parts by weight of L-lactide (manufactured by Musashino Kagaku Kenkyuusho Co., Ltd., optical purity of 100%) to carry out a reaction at 180° C. in a reactor equipped with a stirring blade in a nitrogen atmosphere for 2 hours, phosphoric acid was added as a catalyst deactivator in an amount of 1.2 times the equivalent of tin octylate, the residual lactide was removed at 13.3 Pa, and the residue was formed into a chip to obtain poly(L-lactic acid). The carboxyl group concentration of the obtained poly(L-lactic acid) was 14 eq/ton.

100 parts by weight of the obtained poly (L-lactic acid) and 0.5 part by weight of the cyclic carbodiimide (CC2) were melt kneaded together by means of a double-screw extruder (cylinder temperature of 210° C., residence time of 3 minutes). The carboxyl group concentration of poly(L-lactic acid) dropped to not more than 0.4 eq/ton. There was no smell of an isocyanate at the outlet of the extruder after kneading.

Example 2

End-Sealing of Polylactic Acid by CC1

When a reaction was carried out in the same manner as in Example 1 except that the cyclic carbodiimide (CC2) was changed to the cyclic carbodiimide (CC1), the carboxyl group concentration dropped to not more than 0.7 eq/ton. There was no smell of an isocyanate at the outlet of the extruder after kneading.

Comparative Example 1

End-Sealing of Polylactic Acid by Linear Carbodiimide Compound

When a reaction was carried out in the same manner as in Example 1 except that the cyclic carbodiimide (CC2) was changed to the Stabacsole I linear carbodiimide of Line Chemie Japan Co., Ltd., the carboxyl group concentration was 0.6 eq/ton but a strong bad smell of an isocyanate was produced at the outlet of the extruder.

Example 3

End-Sealing of Polyamide by CC2

Polymetaxylene adipamide (MX Nylon S6001 of Mitsubishi Gas Chemical Co., Ltd.) is a polyamide comprising metaxylylenediamine and adipic acid and had a carboxyl group concentration of 70 eq/ton. 100 parts by weight of this polymetaxylene adipamide and 2.0 parts by of the cyclic carbodiimide compound (CC2) were melt kneaded together by means of a double-screw extruder (cylinder temperature of 260° C., a residence time of 3 minutes). The carboxyl group concentration of polymetaxylene adipamide dropped to not more than 1.5 eq/ton. There was no smell of an isocyanate at the outlet of the extruder after kneading.

Comparative Example 2

End-Sealing of Polyamide by Linear Carbodiimide Compound

When a reaction was carried out in the same manner as in Example 3 except that the cyclic carbodiimide (CC2) was changed to the Stabacsole I linear carbodiimide of Line Chemie Japan Co., Ltd., the carboxyl group concentration was 2.2 eq/ton but a strong bad smell of an isocyanate was produced at the outlet of the extruder.

Effect of the Invention

According to the present invention, an end of a polymer can be sealed with the cyclic carbodiimide compound without liberating an isocyanate compound. As a result, the production of a bad smell from a free isocyanate compound can be suppressed, thereby making it possible to improve the work environment.

When the end of the polymer is sealed with the cyclic carbodiimide compound, an isocyanate group is formed at the end of the polymer, and the molecular weight of the polymer can be increased through a reaction of the isocyanate group.

The cyclic carbodiimide compound also has the function of capturing a free monomer and a compound having an acid group contained in the polymer.

Further, according to the present invention, since the cyclic carbodiimide compound has a cyclic structure, it can seal an end under more mild conditions than those of a linear carbodiimide compound.

The difference between a linear carbodiimide compound and a cyclic carbodiimide compound in end-sealing reaction mechanism is described below.

When the linear carbodiimide compound ($R_1$—N=C=N—$R_2$) is used as an end-sealing agent for a polymer having a terminal carboxyl group, a reaction represented by the following formula takes place. In the formula, W is the main chain of the polymer. An amide group is formed at an end of the polymer through a reaction between the linear carbodiimide compound and the carboxyl group, and an isocyanate compound ($R_1$NCO) is liberated.

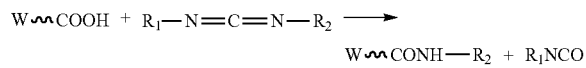

Meanwhile, when the cyclic carbodiimide compound is used as an end-sealing agent for a polymer having a terminal carboxyl group, a reaction represented by the following formula takes place. It is understood that an isocyanate group (—NCO) is formed at an end of the polymer via an amide group through a reaction between the cyclic carbodiimide compound and the carboxyl group and that an isocyanate compound is not liberated.

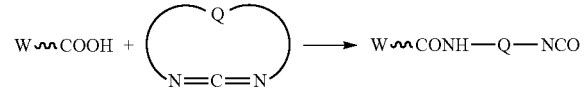

(in the above formula, Q is a divalent to tetravalent bond group which is selected from an aliphatic group, an alicyclic group, an aromatic group or a combination of these and may contain a heteroatom or a substituent.)

Since the cyclic carbodiimide compound used in the present invention has no long chain, it has high heat resistance and can be used to seal an end of a polymer having a high melting point.

INDUSTRIAL APPLICABILITY

The method of the present invention can be used to stabilize a polymer.

The invention claimed is:
1. A method of using a compound including a cyclic structure represented by the following formula (1), comprising providing a compound including at least one cyclic structure represented by the following formula (1) as an end-sealing agent for polymers having at least one acid group selected from the group consisting of carboxyl group, sulfonate group, sulfinate group, phosphonate group and phosphinate group, to suppress production of free isocyanate compound, wherein the number of atoms directly forming the —N=C=N— group-containing ring of the cyclic structure represented by the following formula (1) is 8 to 20,

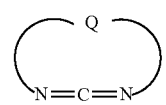 (1)

wherein Q is a divalent to tetravalent bond group represented by the following formula (1-1) or (1-2):

 (1-1)

 (1-2)

wherein $Ar^1$ and $Ar^2$ are each independently a divalent to tetravalent aromatic group having 5 to 15 carbon atoms which may contain a heteroatom or a substituent, $R^1$ and $R^2$ are each independently a divalent to tetravalent aliphatic group having 1 to 20 carbon atoms, a divalent to tetravalent alicyclic group having 3 to 20 carbon atoms, a combination of the aliphatic group and the alicyclic group, or a combination of the aliphatic group, the alicyclic group and a divalent to tetravalent aromatic group having 5 to 15 carbon atoms, wherein the aliphatic group, the alicyclic group, and the aromatic group may contain a heteroatom or a substituent, $X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof, wherein the aliphatic group, the alicyclic group, and the aromatic group may contain a heteroatom or a substituent, s is an integer of 0 to 10, k is an integer of 0 to 10, with the proviso that when s or k is 2 or more, $X^1$ or $X^2$ as a recurring unit may differ from another $X^1$ or $X^2$, respectively, with the proviso that when Q is a divalent bond group, $Ar^1$, $Ar^2$, $R^1$, $R^2$, $X^1$, and $X^2$ are all divalent groups, when Q is a tervalent bond group, one of $Ar^1$, $Ar^2$, $R^1$, $R^2$, $X^1$, and $X^2$ is a tervalent group, and when Q is a tetravalent bond group, one of $Ar^1$, $Ar^2$, $R^1$, $R^2$, $X^1$, and $X^2$ is a tetravalent group, or two of them are tervalent groups, and wherein the substituent is selected from the group consisting of an alkyl group having 1 to 20 carbon atoms, aryl group having 6 to 15 atoms, halogen atom, nitro group, amide group, hydroxyl group, ester group, ether group and aldehyde group.

2. The method according to claim 1, wherein the compound including a cyclic structure is a compound represented by the following formula (2):

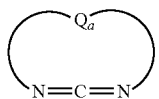
(2)

wherein $Q_a$ is a divalent bond group represented by the following formula (2-1) or (2-2):

$$-Ar_a^1\!-\!(\!O\!-\!X_a^1\!)_s\!-\!O\!-\!Ar_a^2\!- \quad (2\text{-}1)$$

$$-R_a^1\!-\!(\!O\!-\!X_a^2\!)_k\!-\!O\!-\!R_a^2\!- \quad (2\text{-}2)$$

wherein $Ar_a^1$, $Ar_a^2$, $R_a^1$, $R_a^2$, $X_a^1$, $X_a^2$, s and k are identical to $Ar^1$, $Ar^2$, $R^1$, $R^2$, $X^1$, $X^2$, s and k in the above formulas (1-1) to (1-2), respectively.

3. The method according to claim 2, wherein the compound including a cyclic structure is a compound represented by the following formula (2-1-1):

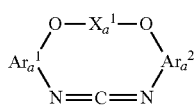
(2-1-1)

wherein $Ar_a^1$ and $Ar_a^2$ are each independently an arylene group having 5 to 15 carbon atoms which may be substituted, and $X_a^1$ is an alkylene group having 1 to 20 carbon atoms.

4. The method according to claim 2, wherein the compound including a cyclic structure is a compound represented by the following formula (2-1-1a):

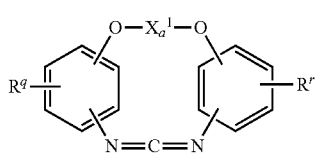
(2-1-1a)

wherein $R^q$ and $R^r$ are each independently a hydrogen atom or an alkyl group having 1 to 20 carbon atoms, and $X_a^1$ is an alkylene group having 1 to 20 carbon atoms.

5. The method according to claim 1, wherein the compound including a cyclic structure is a compound represented by the following formula (3):

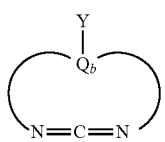
(3)

wherein $Q_b$ is a tervalent bond group represented by the following formula (3-1) or (3-2):

$$-Ar_b^1\!-\!(\!O\!-\!X_b^1\!)_s\!-\!O\!-\!Ar_b^2\!- \quad (3\text{-}1)$$

$$-R_b^1\!-\!(\!O\!-\!X_b^2\!)_k\!-\!O\!-\!R_b^2\!- \quad (3\text{-}2)$$

wherein $Ar_b^1$, $Ar_b^2$, $R_b^1$, $R_b^2$, $X_b^1$, $X_b^2$, s and k are identical to $Ar^1$, $Ar^2$, $R^1$, $R^2$, $X^1$, $X^2$, s and k in the above formulas (1-1) to (1-2), respectively, with the proviso that one of them is a tervalent group, and Y is a single bond, a double bond, an atom, an atom group or a polymer.

6. The method according to claim 1, wherein the compound including a cyclic structure is a compound represented by the following formula (4):

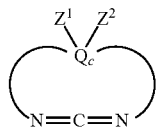
(4)

wherein $Z^1$ and $Z^2$ are each independently an atom, an atom group or a polymer, and $Q_c$ is a tetravalent bond group represented by the following formula (4-1) or (4-2):

$$-Ar_c^1\!-\!(\!O\!-\!X_c^1\!)_s\!-\!O\!-\!Ar_c^2\!- \quad (4\text{-}1)$$

$$-R_c^1\!-\!(\!O\!-\!X_c^2\!)_k\!-\!O\!-\!R_c^2\!- \quad (4\text{-}2)$$

wherein $Ar_c^1$, $Ar_c^2$, $R_c^1$, $R_c^2$, $X_c^1$, $X_c^2$, s and k are identical to $Ar^1$, $Ar^2$, $R^1$, $R^2$, $X^1$, $X^2$, s and k in the above formulas (1-1) to (1-2), respectively, with the proviso that one of them is a tetravalent group, or two of them are tervalent groups.

7. The method according to claim 6, wherein the compound including a cyclic structure is a compound represented by the following formula (4-1-1):

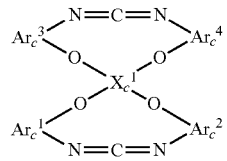
(4-1-1)

wherein $X_c^1$ is an alkanetetrayl group having 1 to 20 carbon atoms, and $Ar_c^1$, $Ar_c^2$, $Ar_c^3$ and $Ar_c^4$ are each independently an arylene group having 5 to 15 carbon atoms which may be substituted with an alkyl group having 1 to 20 carbon atoms.

8. The method according to claim 6, wherein the compound including a cyclic structure is a compound represented by the following formula (4-1-1c):

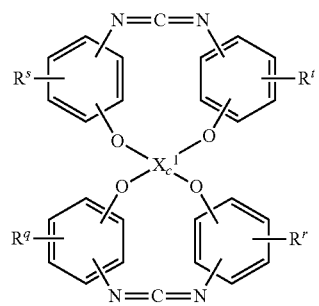
(4-1-1c)

wherein $X_c^1$ is an alkanetetrayl group having 1 to 20 carbon atoms, and $R^q$, $R^r$, $R^s$ and $R^t$ are each independently a hydrogen atom or an alkyl group having 1 to 20 carbon atoms.

9. The method according to claim 1, wherein the polymer is at least one selected from the group consisting of a polyester, a polyamide and a polyimide.

10. The method according to claim 1, wherein the polymer is polylactic acid.

11. The method according to claim 10, wherein the polylactic acid is poly(L-lactic acid).

12. The method according to claim 1, wherein $Ar^1$ and $Ar^2$ are each independently a divalent to tetravalent aromatic group having 5 to 15 carbon atoms which contains a heteroatom or a substituent.

13. The method according to claim 1, wherein $Ar^1$ and $Ar^2$ are each independently a divalent to tetravalent aromatic group having 5 to 15 carbon atoms which does not contain a heteroatom or a substituent.

14. A method of suppressing the production of a free isocyanate compound when the acid group of a polymer having an acid group is sealed, comprising suppressing the production of a free isocyanate compound when the acid group of a polymer having an acid group is sealed by adding a compound having a carbodiimide group,
wherein a compound including a cyclic structure is used as the compound having a carbodiimide group,
wherein the cyclic structure is represented by the following formula (1), wherein the number of atoms directly forming the —N=C=N— group-containing ring of the cyclic structure represented by the following formula (1) is 8 to 20:

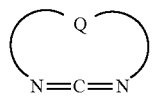

(1)

wherein Q is a divalent to tetravalent bond group represented by the following formula (1-1) or (1-2):

 (1-1)

 (1-2)

wherein $Ar^1$ and $Ar^2$ are each independently a divalent to tetravalent aromatic group having 5 to 15 carbon atoms which may contain a heteroatom or a substituent, $R^1$ and $R^2$ are each independently a divalent to tetravalent aliphatic group having 1 to 20 carbon atoms, a divalent to tetravalent alicyclic group having 3 to 20 carbon atoms, a combination of the aliphatic group and the alicyclic group, or a combination of the aliphatic group, the alicyclic group and a divalent to tetravalent aromatic group having 5 to 15 carbon atoms, wherein the aliphatic group, the alicyclic group, and the aromatic group may contain a heteroatom or a substituent, $X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof, wherein the aliphatic group, the alicyclic group, and the aromatic group may contain a heteroatom or a substituent, s is an integer of 0 to 10, k is an integer of 0 to 10, with the proviso that when s or k is 2 or more, $X^1$ or $X^2$ as a recurring unit may differ from another $X^1$ or $X^2$, respectively, with the proviso that when Q is a divalent bond group, $Ar^1$, $Ar^2$, $R^1$, $R^2$, $X^1$, and $X^2$ are all divalent groups, when Q is a tervalent bond group, one of $Ar^1$, $Ar^2$, $R^1$, $R^2$, $X^1$, and $X^2$ is a tervalent group, and when Q is a tetravalent bond group, one of $Ar^1$, $Ar^2$, $R^1$, $R^2$, $X^1$, and $X^2$ is a tetravalent group, or two of them are tervalent groups, and wherein the substituent is selected from the group consisting of an alkyl group having 1 to 20 carbon atoms, aryl group having 6 to 15 atoms, halogen atom, nitro group, amide group, hydroxyl group, ester group, ether group and aldehyde group.

15. The method according to claim 14, wherein the polymer having an acid group and the compound including a cyclic structure are melt kneaded together for 0.1 minute to 2 hours.

* * * * *